United States Patent
Sayfan et al.

(10) Patent No.: US 10,466,217 B1
(45) Date of Patent: Nov. 5, 2019

(54) METHOD TO COMBINE PARTIALLY AGGREGATED SENSOR DATA IN A DISTRIBUTED SENSOR SYSTEM

(71) Applicant: Aclima Inc., San Francisco, CA (US)

(72) Inventors: Gigi Sayfan, Davis, CA (US); Stanley Hu, San Francisco, CA (US)

(73) Assignee: Aclima Inc., San Francisco, CA (US)

( * ) Notice: Subject to any disclaimer, the term of this patent is extended or adjusted under 35 U.S.C. 154(b) by 1247 days.

(21) Appl. No.: 14/139,769

(22) Filed: Dec. 23, 2013

(51) Int. Cl.
*G01N 33/00* (2006.01)

(52) U.S. Cl.
CPC ................ *G01N 33/0009* (2013.01)

(58) Field of Classification Search
CPC ........ G06F 17/30985; G06F 17/30864; G01N 1/26; G01N 33/0009; G06Q 10/087; H04L 45/00; H04L 29/12066
USPC ........... 707/693; 711/170; 700/275; 370/252, 370/392
See application file for complete search history.

(56) References Cited

U.S. PATENT DOCUMENTS

| | | | |
|---|---|---|---|
| 5,428,776 A | 6/1995 | Rothfield | |
| 6,128,617 A | 10/2000 | Lowry | |
| 6,399,391 B1 | 6/2002 | Tomlin | |
| 6,941,193 B2 | 9/2005 | Frecska | |
| 7,146,356 B2 | 12/2006 | Choi et al. | |
| 7,188,090 B2 | 3/2007 | Kim et al. | |
| 7,302,313 B2 * | 11/2007 | Sharp | G01N 1/26 700/275 |
| 7,302,331 B2 * | 11/2007 | Meyers | B60G 17/0162 303/138 |
| 7,849,048 B2 | 12/2010 | Langseth et al. | |
| 8,289,992 B2 | 10/2012 | Fujiwara et al. | |
| 8,294,715 B2 | 10/2012 | Patel et al. | |
| 8,326,662 B1 | 12/2012 | Byrne et al. | |
| 8,355,981 B2 | 1/2013 | West | |
| 8,370,386 B1 | 2/2013 | Wang et al. | |
| 8,395,625 B2 | 3/2013 | Buck | |
| 8,953,472 B2 | 2/2015 | Di Pietro et al. | |
| 9,276,716 B2 | 3/2016 | Wetterwald et al. | |
| 2002/0128998 A1 | 9/2002 | Kil et al. | |
| 2004/0233855 A1 * | 11/2004 | Gutierrez | H04L 45/00 370/252 |
| 2007/0268128 A1 * | 11/2007 | Swanson | H04Q 9/00 340/539.22 |

(Continued)

FOREIGN PATENT DOCUMENTS

EP        0797162        9/1997

OTHER PUBLICATIONS

Madden et al., "Fjording the Stream: An Architecture for Queries over Streaming Sensor Data", IEEE 2002, 12 pages.

*Primary Examiner* — Regis J Betsch
*Assistant Examiner* — Kaleria Knox
(74) *Attorney, Agent, or Firm* — Van Pelt, Yi & James LLP

(57) ABSTRACT

A method for processing sensor data in a distributed sensor system includes generating aggregated sensor data values associated with a first sensor and belonging to one or more aggregation time intervals, tagging each aggregated sensor data value with an aggregation indicator. The aggregation indicator has a first value indicating partial aggregation and has a second value indicating complete aggregation. In some embodiments, the method combines the partially aggregated sensor data belonging to the same time interval into a complete aggregated sensor data.

18 Claims, 10 Drawing Sheets

(56) References Cited

U.S. PATENT DOCUMENTS

| | | | |
|---|---|---|---|
| 2008/0320128 A1 | 12/2008 | Bou-Diab et al. | |
| 2009/0085769 A1* | 4/2009 | Thubert | H04L 45/04 340/870.07 |
| 2009/0172090 A1 | 7/2009 | Lit | |
| 2009/0193217 A1* | 7/2009 | Korecki | G06Q 10/087 711/170 |
| 2009/0262741 A1* | 10/2009 | Jungck | H04L 29/12066 370/392 |
| 2011/0320136 A1 | 12/2011 | Sunshine et al. | |
| 2012/0197911 A1* | 8/2012 | Banka | G06F 17/30864 707/752 |
| 2013/0103657 A1* | 4/2013 | Ikawa | G06F 17/30985 707/693 |
| 2013/0159454 A1 | 6/2013 | Hunter | |
| 2015/0127284 A1 | 5/2015 | Seshan | |

\* cited by examiner

Aggregated Sensor Data Document     ─ 250

Node ID (MAC address): '20716411288L'

Loc ID: '266'

Agg ID: 'owl-00'

Sensor ID: '-67225787104L'

Minute: '2013-09-11 11:14:43-0000'

Period: '20130911'

Readings: [ pct_avg : 20.79734723729,
           pct_avg_sum : 1247.840834237,
           pct_max : 20.90638406,
           pct_min : 20.636942243,
           raw_avg : 18027.28333333,
           raw_avg_sum : 1081637,
           raw_max : 18041,
           raw_min : 18015,
           samples : 60,
           timestamp : '2013-09-11 11:14:43-0000']

FIG. 5

Sensor Data Query — 430

| Locations | Location Types | Sensor Types | Time Range |

Locations

| Cities | Buildings | Rooms |
|---|---|---|
| City1 | BuildingA | Room1 |
| City2 | BuildingB | Room2 |
| City3 | BuildingC | Room3 |

Location Types
Hallway
Office
Outdoor
Gym
Conference Room
Cafeteria

Sensors
$CO_2$
$O_2$
CO
$NO_2$
Humidity
Light
Temperature
Sound

Time Range
Now (Last 60 minutes)
Yesterday
Last 7 Days
Last Week
Last Month

Start time:
End Time:

Query | Sign Out

FIG. 8

METHOD TO COMBINE PARTIALLY AGGREGATED SENSOR DATA IN A DISTRIBUTED SENSOR SYSTEM

BACKGROUND OF THE INVENTION

Environmental monitoring, sensing and measurements have become of interest to enterprises and individuals wishing to assess the current conditions of the environment in which individuals live or work or to characterize and monitor the quality of the environment. In some cases, environmental monitoring is performed to establish trends in environmental parameters, such as for detecting operations of building heating and cooling systems or operation of factory machinery. In other cases, environmental monitoring may be performed for detecting climate changes. Environment sensing and measurements can include air quality monitoring, water quality monitoring, and monitoring of other environment factors.

Air quality is a measure of the condition of air relative to the requirements of human need or purpose. Outdoor air quality monitoring is performed to measure the levels of pollutants in the air so as to detect potential harmful air pollution. Outdoor air quality monitoring is typically carried out using monitoring station installations in various physical locations. These monitoring stations measure the presence of contaminants in the air, such as carbon monoxide, ozone, particulate matter, sulphur dioxide ($SO_2$) and carbon dioxide ($CO_2$). Indoor air quality monitoring is becoming a matter of interest as the air in enclosed spaces, such as home, schools or workplaces, can also be polluted. Conventional air quality monitors are expensive and require complex calibration procedure to ensure accurate measurements.

BRIEF DESCRIPTION OF THE DRAWINGS

Various embodiments of the invention are disclosed in the following detailed description and the accompanying drawings.

FIG. 5 illustrates an example of a sensor data document for storing aggregated sensor data in the central server in embodiments of the present invention.

FIGS. 8, 9 and 10 illustrate a user interface for performing sensor data query using the sensor data query method according to embodiments of the present invention.

DETAILED DESCRIPTION

Figure 1:
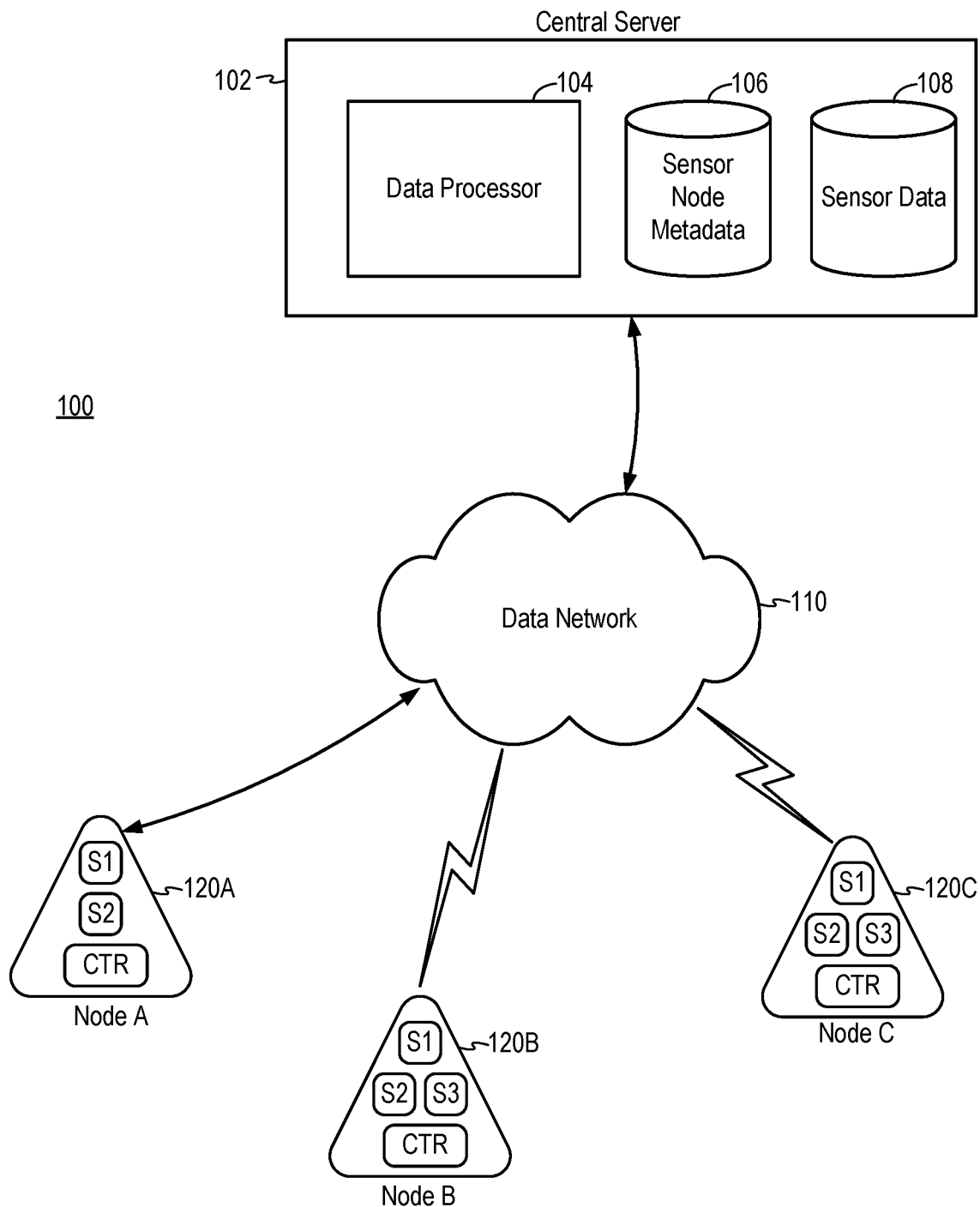
FIG. 1 is a system diagram illustrating an embodiment of a distributed sensor system for measuring air quality in an environment.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

A data collection system and method is implemented in a distributed sensor system to facilitate the collection of sensor data generated from multiple sensors deployed in the field. The sensors may be numerous and may be deployed over a wide geographic area. The sensors communicate with a central server over a data network and transmit continuous real-time sensor data to the central server. The data collection system and method is configured to receive the continuous real-time sensor data from multiple data sources and process the large volume of sensor data. Furthermore, the data collection system and method processes and stores the sensor data to enable fast query of the sensor data. In some embodiments, the sensor data is stored using multi-level aggregation that allows the sensor data to be queried efficiently and quickly.

In some embodiments, the data collection system and method of the present invention implements scalable distributed stateless processing to enable the data collection system to be scaled up easily as additional sensors are deployed in the distributed sensor system. Thus, the distributed sensor system can be expanded by deployment of additional sensors and the data collection system can be readily scaled up to handle the increased volume of continuous real-time sensor data.

Distributed Sensor System

FIG. 1 is a system diagram illustrating an embodiment of a distributed sensor system for measuring air quality in an environment. An example of the distributed sensor system is also described in copending and commonly assigned U.S. patent application Ser. No. 13/800,172, filed Mar. 13, 2013, entitled "Distributed Sensor System With Remote Sensor Nodes And Centralized Data Processing," of Risk et al, which application is incorporated herein by reference in its entirety. Referring to FIG. 1, a distributed sensor system 100 including a set of spatially distributed base units 120, also referred to as "sensor nodes" or "nodes," configured to obtain measurements from the environment. In FIG. 1, sensor nodes A to C (120A to 120C) are shown. The sensor nodes in system 100 may be deployed in an indoor location or an outdoor location or both for monitoring the local air quality. In some embodiments, a set of sensor nodes are strategically deployed in a location to obtain sufficient amount of measurements to assess the air quality in a location. For example, in one embodiment, a set of sensor nodes are spatially dispersed in a building, such as a workplace or a factory, to monitor the air quality in the building.

Each base unit 120 includes one or more sensor modules (S#) and a controller (CTR) which incorporates therein a transceiver. A sensor module S# incorporates a sensor for detecting a specific air quality parameter. The sensor modules may include different types of sensors for sensing different air quality parameters. A set of base units 120 deployed in an installation may be configured with sensor modules with the same sensor type. For example, nodes A, B and C all include sensor modules S1 and S2. A set of base units 120 may also be configured with sensor modules with different sensor types. For example, nodes B and C include the sensor module S3 and not Node A. A salient feature of the base unit 120 in the distributed sensor system of the present invention is that the base unit is configurable to allow any desired types of sensors to be incorporated for measuring the desired environment parameters. Thus, a set of nodes for an installation can be configured with the same set of sensor modules to measure the same set of air quality parameters. Alternately, a set of nodes for an installation can be configured with different sensor modules to measure a different set of air quality parameters at each node. In one example, the types of sensors that can be included in a base unit include $CO_2$, $O_2$, CO, $CH_2O$, $NO_2$, Particulate Matter, Volatile Organic Compound (VOC), Humidity, Light, Temperature, Sound, and Vibration.

Each of the base units 120 includes a transceiver to communicate with a central server 102 through a data network 110. The base units 120 may employ wired communication, such as Ethernet, or wireless communications, such as radio frequency (RF), WiFi, ZigBee or other low power short-range wireless communication protocols. The controller CTR controls the sensing and communication functions of the base unit. The data network 110 may include a private data network, the public Internet, or a combination of both. In embodiments of the present invention, the central server 102 may be implemented using one or more computing systems or one or more server appliances. Implementing the central server 102 using multiple server appliances improves the reliability of the system. In the present description, the term "central server" refers to a computing unit, which can be physical or logical, for performing the data processing and storage functions described herein where the central server can be implemented using one or more server appliances.

Central server 102 includes a data processor 104, a sensor node metadata database 106 stored in a computer data storage or memory, and a sensor data database 108 stored in a computer data storage or memory. The sensor node metadata database 106 stores management data or metadata associated with each sensor nodes in system 100. The metadata includes identification information for the sensor node, such as a Node Identifier or a serial number. The metadata also includes calibration data for the sensor in each base unit. Central server 102 stores in the sensor data database 108 raw sensor data received from the base units 120 over the data network 110. Data processor 104 is configured to process the raw sensor data using the calibration data stored in the sensor node metadata database 106 to generate calibrated sensor data which can then be used to assess the air quality at the installation where sensor nodes 120 are deployed. The calibrated sensor data may also be stored in the sensor data database 108. The calibrated sensor data, as well as the raw sensor data, may be accessible through one or more application programming interface (API) to allow users to monitor the air quality measurements obtained by the distributed sensor system 100.

Another salient feature of the distributed sensor system of the present invention is that each sensor module provides raw sensor data to the central server to be stored and processed. In the present description, raw sensor data refers to sensor data that has not been modified or calibrated based on performance characteristics of the particular sensor that generated the sensor data. Most sensors have certain amount of non-linearity characteristics over time and sensors need to be calibrated for the non-linearity or performance drift over time. Typically, a sensor may have gain or offset that drifts over time as the sensor is being used in an environment.

Conventional sensors are often calibrated periodically, such as annually, and the calibration data, such as a gain correction value and an offset correction value, for the sensor is stored with the sensor itself and sensor data is modified using the calibration data as the sensor data is being generated by the sensor. In the conventional sensors, when a sensor's characteristics drift over time before the next calibration update, the calibration data may no longer be accurate for that sensor. However, the sensor will continue to use the inaccurate calibration data to calibrate or modify the sensor data. Thus, conventional sensors may end up generating sensor data that has embedded calibration error and the sensor data is permanently corrupted. In some examples, the distributed sensor system 100 implements a centralized backend calibration method where the base unit 120 reports raw sensor data that have not been modified to the central server 102. Calibration of the raw sensor data is performed at the central server 102 to generate calibrated sensor data using calibration data stored at the central server. The availability of the raw sensor data allows the central server to generate calibrated sensor data using updated or corrected calibration data so that accuracy of the sensor measurement can be assured. More importantly, when calibration data for a sensor is found to be inaccurate later on and new calibration data is generated, the central server may regenerate the calibrated sensor data by retrieving the raw sensor data for that sensor and calibrating the raw sensor data again using updated calibration data. In this manner, historic sensor data can be corrected if the calibration data used was found to be inaccurate. Correction of historic sensor data is not possible in conventional sensors because the calibration was done at the sensor and raw sensor data is typically not available. The centralized backend calibration method in the distributed sensor system of the present invention is described in copending and commonly assigned U.S. patent application Ser. No. 13/800,199, filed Mar. 13, 2013, entitled "Calibration Method For Distributed Sensor System," of Herzl et al., which application is incorporated herein by reference in its entirety.

In FIG. 1, the sensor calibration data (or sensor metadata) and the sensor data are shown as being stored in two databases. The two databases can be two physical databases or two logical databases. The exact configuration of the two databases is not critical to the practice of the present invention. The storage of the sensor metadata and the sensor data can be made in one physical data storage or multiple physical data storages.

Data Collection Engine

In the distributed sensor system 100, sensor data are being generated at a high data rate from each sensor deployed in the installation. For example, sensor data is generated every second. In a typical installation, a large number of nodes, each with multiple sensors, may be deployed. Thus, the distributed sensor system 100 generates a high volume of data at a high data rate. For example, for an installation with 500 nodes each with 12 sensors, a total of 6000 sensors is deployed in the system. When each sensor generates sensor data every second, 6000 sensor data messages are being generated every second. The data collection system and method of the present invention is configured to receive and process the high volume of sensor data generated at the high data rate to support the operation of the distributed sensor system 100.

Figure 2:
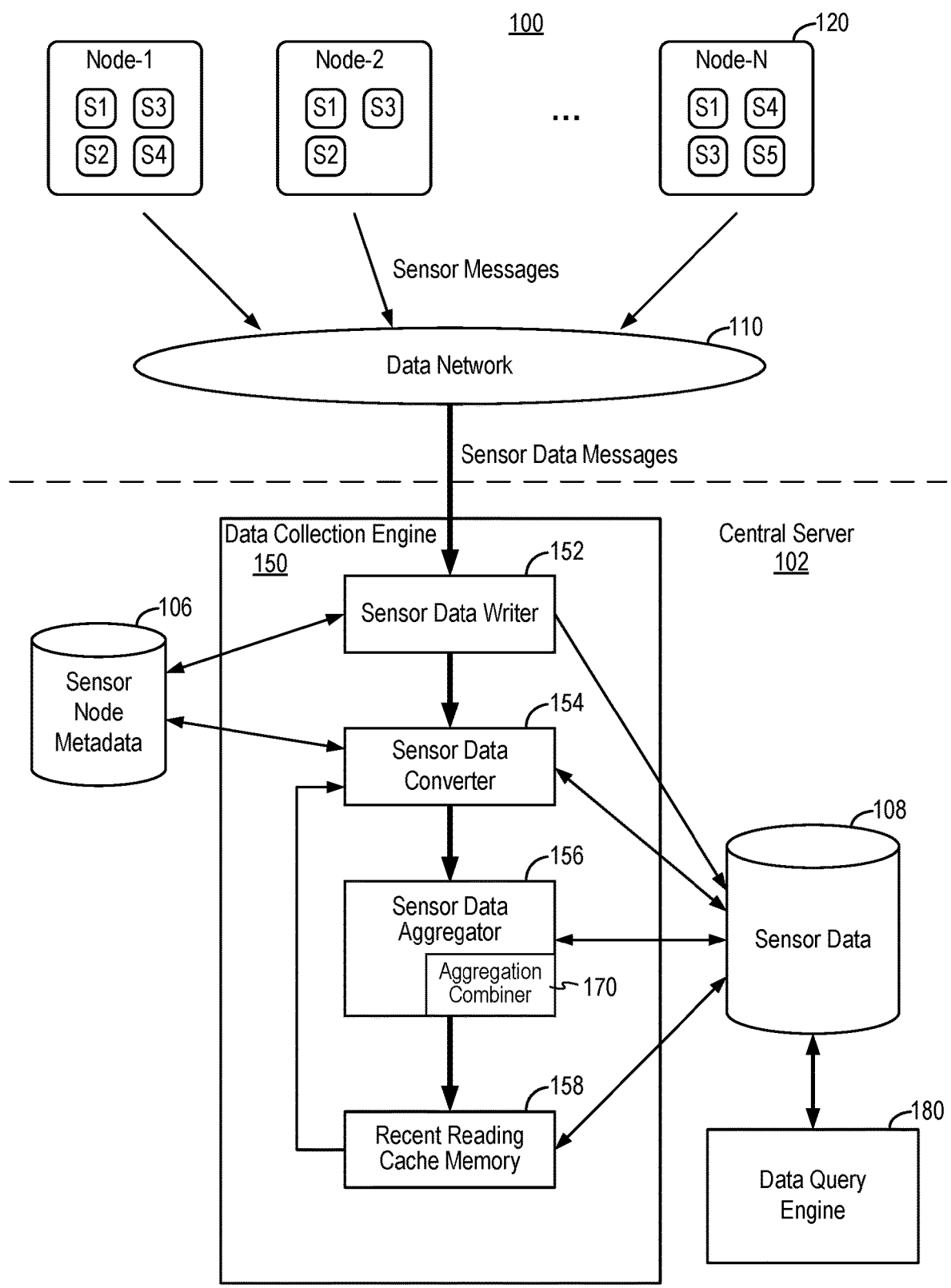
FIG. 2 is a block diagram illustrating a data collection engine in the central server of the distributed sensor system in embodiments of the present invention.

FIG. 2 is a block diagram illustrating a data collection engine in the central server of the distributed sensor system in embodiments of the present invention. Referring to FIG. 2, in the distributed sensor system, a set of sensor nodes 120 is deployed in an installation to measure air quality parameters. The sensor nodes 120 may be deployed within a building or over several buildings. In some examples, the sensor nodes 102 may be deployed in a corporation's workplaces in several countries over several continents. Each sensor node 120 includes one or more sensor modules containing a sensor. A sensor module or sensor (S#) is provided for detecting a specific air quality parameter. Additional sensors may be included for measuring environmental qualities, such as temperature, humidity, pressure and ambient light condition. In the present example, the sensors nodes Node-1 to Node-N may include different type of sensors to sense different air quality parameters and environmental parameters. Each sensor node 120 is configured to send sensor messages to the central server 102 through the data network 110. The sensor messages may include sensor management messages and sensor data messages. Sensor management messages may be sent for set up and configuration of the sensor module and the sensor node. The data collection system and method of the present invention is concerned with receiving and processing the sensor data messages that are sent by each sensor module to report sensor readings.

In embodiments of the present invention, each sensor in a sensor node 120 sends a periodic sensor data message to report the sensor's recent readings. The sensor data message includes identifying information for the sensor including a Node identifier (Node ID) identifying the sensor node, a controller board identifier (Board ID) identifying the controller board in the sensor node, a sensor identifier (Sensor ID) identifying each sensor in a sensor node. In some embodiments, the identifying information may further includes a sensor type identifier (Sensor Type ID) to identify the type of sensor (e.g. $CO_2$, $O_2$ or humidity). In some cases, the separate Sensor Type ID is not needed and the Sensor ID provides the identification of the type of sensor as well as the specific sensor reporting sensor data.

The sensor data message further includes sensor readings for that sensor represented in raw sensor data values. Each sensor is configured to report sensor data on a periodic basis, referred herein as a reporting interval or a reporting period. For example, the reporting period may be once per second or 1 Hz. However, in some cases, the sensor incorporated in a node may be capable of sampling the environment at a frequency greater than the reporting period. For example, while the reporting period may be 1 Hz or once per second, the sensor may be capable of sampling at a rate of 60 Hz, that is, 60 times per second. In embodiments of the present invention, each sensor reports at each reporting interval the sensor readings collected during that interval. For example, in one embodiment, the sensor data message includes a sensor data set which includes a maximum sensor reading, a minimum sensor reading, and the average sensor reading of the sensor readings generated during the reporting interval. The sensor readings reported in the sensor data message are raw sensor data. The raw sensor data may be generated from analog or digital sensor readings which may be a current value or a voltage value. In most cases, the sensor module includes an analog-to-digital converter to digitize analog sensor readings to generate the raw sensor data value.

In the distributed sensor system 100, each sensor in each sensor node sends periodic sensor data messages to the central server 102 through the data network 100. Thus, the central server 102 receives a large amount of sensor data messages arriving at each reporting intervals, such as each second. In embodiments of the present invention, the central server 102, incorporates a data collection system for receiving and processing the sensor data messages. In the present embodiment, the data collection system is implemented as a data collection engine 150 which can include software or hardware components or a combination of software and hardware components. Data collection engine 150 is in communication with the sensor node metadata database 106 to receive calibration data and other metadata associated with each sensor reading. The data collection engine 150 is also in communication with the sensor data database 108 to retrieve and store raw and processed sensor data.

In the present example, the sensor node metadata database 106 is implemented using a relational database, such as a SQL database. The relational database allows the sensor node metadata to be retrieved quickly when requested. Also, in the present embodiment, the sensor data database 108 is implemented as a non-SQL document database. The sensor data database 108 has to store a large amount of data and a non-relational or non-SQL database is more efficient.

In embodiments of the present invention, the data collection engine 150 includes a sensor data writer 152 configured to receive the sensor data messages sent to the central server 102 over the data network 110. The sensor data writer 152 performs decoding of the sensor data messages to obtain the identifying information and the raw sensor data from the sensor data message. The sensor data writer 152 may be in communication with the sensor node metadata database 106 to receive sensor node information. The sensor data writer 152 also sends the decoded raw sensor data with the identify information (such as Node ID and Sensor ID) to the sensor data database 108 for storage.

The data collection engine 150 includes a sensor data converter 154 to process the decoded raw sensor data. The sensor data converter 154 is in communication with the sensor node metadata database 106 to receive calibration data. More specifically, the sensor data converter 154 processes the raw sensor data to convert the sensor readings to meaningful physical units and also to calibrate the raw sensor data using the calibration data for that sensor retrieved from the sensor node metadata database 106. The calibrated sensor data is stored in the sensor data database 108. In some embodiments, the raw sensor data and the calibrated sensor data are stored in the sensor data database in the same document. For instance, the raw sensor data is typically expressed as a numeric string. The sensor data converter 154 converts the numeric string to a sensor data value having a physical unit for that sensor type. For example, the sensor data value may have a physical unit of ppm or percentage for air quality parameters or degree Celsius for temperature. The converted sensor data is then calibrated using the calibration data for that sensor.

In some embodiments, the sensor data calibration is performed using the calibration data for that sensor and also the temperature and humidity values taken at the sensor node concurrently with the sensor reading or within the same time frame as the sensor reading. Furthermore, in some cases, sensor data calibration also uses the air pressure value in addition to the temperature and humidity values. For example, the current temperature and humidity values can be retrieved from the sensor data database 108 as the sensor data for temperature and humidity is also continuously received and processed and stored in the sensor data database. In some embodiments, the calibration of the sensor data is performed using aggregated or summarized temperature and/or humidity data for the previous minute or previous 10 minutes. The aggregated or summarized temperature and humidity data may be retrieved from the sensor data database or from another local storage. The generation of aggregated and summarized sensor data values will be described in more detail below. By incorporating temperature and humidity experienced by the sensors into the calibration process, the accuracy of the sensor calibration can be greatly improved.

In other embodiments, the sensor data calibration is performed using sensor data of neighboring sensors taken concurrently to eliminate sensor cross-sensitivity. For example, a formaldehyde sensor (HCHO) is also sensitive to carbon monoxide (CO) in the atmosphere. Calibration of the HCHO sensor can use the CO sensor data values taken concurrently to mitigate the effects of cross-sensitivity. For example, the HCHO sensor data can be calibrated by subtracting out a CO measurement taken concurrently. In some embodiments, the sensor data calibration is performed using cross-sensitivity sensor data in addition to temperature and humidity data. In some embodiments, the current cross-sensitivity sensor data values can be retrieved from the sensor data database 108 as the cross-sensitivity sensor data is continuously received and processed and stored in the sensor data database. In some embodiments, the calibration of the sensor data is performed using aggregated or summarized cross-sensitivity sensor data for the previous minute or previous 10 minutes. The aggregated or summarized cross-sensitivity sensor data may be retrieved from the sensor data database or from another local storage. The generation of aggregated and summarized sensor data values will be described in more detail below. By incorporating cross-sensitivity sensor data experienced by the sensors into the calibration process, the accuracy of the sensor calibration can be greatly improved.

The data collection engine 150 further includes a sensor data aggregator 156 which generates aggregated sensor data for each sensor over one or more predetermined time intervals. In some embodiments, the sensor data aggregator 156 generates sensor data using multi-level aggregation to allow the sensor data to be queried efficiently and quickly. In operation, the sensor data aggregator 156 is in communication with the sensor data converter 154 to receive sensor data and also is in communication with the sensor data database 108 to receive sensor data and to store aggregated sensor data. In embodiments of the present invention, the sensor data aggregator 156 performs two types of sensor data aggregation. First, the sensor data aggregator 156 performs initial sensor data aggregation using the calibrated sensor data from the sensor data converter 154. More specifically, the sensor data aggregator 156 aggregates sensor data at one or more low aggregation levels using the calibrated sensor data. For example, raw sensor data may be received from the sensors in the field on a 1-second interval and processed by the sensor data converter 154 at the 1-second interval. The sensor data aggregator 156 may aggregate the calibrated sensor data for each sensor over one or more low-level time intervals, such as a 1-minute interval and/or a 5-minute interval. In the present description, aggregation of sensor data of a sensor over a given time interval refers to averaging all of the sensor data of a sensor belonging to that time interval. Accordingly, when sensor data from a sensor is received on a 1-second interval, 1-minute sensor data may be generated by aggregating or averaging all the 1-second sensor data during each 1 minute interval.

In one embodiment, the sensor data aggregator 156 performs initial sensor data aggregation at a first aggregation level of 1-minute interval. The sensor data aggregator 156 receives calibrated sensor data on a 1-second interval and stores the calibrated sensor data in a local memory until the sensor data aggregator 156 starts receiving sensor data from the next minute. Then, the sensor data aggregator 156 computes the aggregated sensor data value for all of the 1-second sensor data in the previous minute interval to generate the 1-minute sensor data. The computed 1-minute sensor data is then stored in the sensor data database 108. In other embodiments, the initial sensor data aggregation may generate aggregated sensor data at two or more low aggregation levels, such as 1-minute and 5-minute intervals.

With aggregated sensor data thus generated at one or more low aggregation levels, the sensor data aggregator 156 performs high-level sensor data aggregation using the low-level aggregated sensor data stored in the sensor data database 108. More specifically, the sensor data aggregator 156 aggregates the previously aggregated sensor data to generate aggregated sensor data at one or more high aggregation levels. High-level sensor data aggregation may be performed for a range of time intervals, for example, 10-minute interval, 1-hour interval, 8-hour interval and 1-day interval. Furthermore, the sensor data aggregator 156 generates high-level aggregated sensor data using low-level aggregated sensor data. For example, 10-minute sensor data may be generated by aggregating or averaging the 1-minute sensor data during each 10 minute interval, and 1-hour sensor data may be generated by aggregating or averaging the 10-minute sensor data. In one embodiment, when the sensor data aggregator 156 receives calibration sensor data for a new 10-minute interval, the sensor data aggregator 156 retrieves the 1-minute sensor data for the previous 10-minute interval from the sensor data database 108 and aggregates the 1-minute sensor data to generate the 10-minute sensor data. For example, the aggregation of the 10-minute sensor data for the interval 9:20 am to 9:30 am will start when sensor data with timestamp later than 9:30 am arrives at the sensor data aggregator 156. The same operation can be repeated to generate aggregated sensor data for other high aggregation levels. For example, the 1-hour aggregated sensor data can be generated when sensor data for a new hour arrives at the sensor data aggregator 156. The 1-hour aggregated sensor data can be generated from the aggregated 10-minute data for the previous hour.

In the above described embodiments, the sensor data aggregator 156 receives sensor data from the sensor data converter 154 and from the sensor data database 108. In practice, the operation of the sensor data aggregator 156 is agnostic as to where the sensor data is being retrieved from. The sensor data aggregator 156 may obtain recent sensor data from the sensor data converter 154 and stores the sensor data in a local memory. The sensor data aggregator 156 may store older sensor data in a memory buffer of a local software process, or in an in-memory database, such as Redis, or in a memory buffer with NoSQL database. In other examples, the sensor data aggregator 156 may obtain sensor data from a traditional disk-based database. The exact nature of the memory storage for sensor data to be aggregated is not critical to the practice of the present invention.

In some embodiments, the sensor data aggregator 156 runs continuously at several increasing time intervals, such as 1-minute interval, 10-minute interval and 1-hour interval. In one example, the sensor data aggregator 156 aggregates at the following intervals: 1 minute, 10 minutes, 1 hour, 8 hours and 1 day. Furthermore, daily and weekly intervals may also be used to aggregate sensor data on a daily basis or weekly basis. Furthermore, in embodiments of the present invention, the sensor data aggregator 156 uses previously aggregated sensor data of a smaller time interval (low aggregation level) to generate aggregated sensor data for a larger time interval (high aggregation level). For instance, the sensors in the sensor nodes 120 may be configured to report sensor readings on a 1-second interval. The sensor data aggregator 156 may run continuously at each minute interval, each 10-minute interval and each hour interval to generate aggregated sensor data. The aggregated sensor data generated at each time interval, such as the 1-minute data, the 10-minute data, and the 1-hour data, are stored in the sensor data database 108. Furthermore, to generate the 10-minute data, the sensor data aggregator 156 retrieves the 1-minute data for the previous 10 minutes from the sensor data database 108 and computes the 10-minute data using the previously aggregated 1-minute data. Similarly, to generate the 1-hour data, the sensor data aggregator 156 retrieves the 10-minute data for the previous 60 minutes from the sensor data database 108 and computes the 1-hour data using the previously aggregated 10-minute data.

In embodiments of the present invention, the sensor data aggregator 156 stores aggregated sensor data in the sensor data database in a document format. The aggregated sensor data is stored with a sensor data set including a maximum sensor data value, a minimum sensor data value, and the average sensor data value of the aggregated data values over the aggregation time interval. Furthermore, the aggregated sensor data may be stored with the sum of the sensor data values being aggregated and the sample size. The sum of the sensor data values can be advantageously applied to generate higher-level aggregated sensor data using a lower-level aggregated sensor data. For example, to generate 1-hour data from the 10-minute data, the sensor data aggregator 156 can use the sum values and the sample size for all the 10-minute data. The computation burden is significantly reduced. Including the sum of the sensor data values and the sample size with the sensor data also provides the benefit of allowing the sensor data to be easily recalculated at a later time, such as when the calibration data for the sensor has been updated.

Performing sensor data aggregation at the data collection engine 150 and storing multi-level aggregated sensor data at the central server 102 provides particular advantages when the sensor data is to be accessed or queried at a later time. In the distributed sensor system, the sensors in the sensor nodes generate sensor readings at a higher data rate that may be of interest in practice. For example, the sensors may be reporting sensor data at a 1-second reporting interval (1 Hz). However, in actual practice, a user may not be interested in sensor data at such small temporal granularity. Although the central server can store incoming sensor data at the high data rate, a user may wish to examine the sensor data using a larger temporal granularity. For example, the user may be interested in sensor readings on an hourly interval as opposed to 1-second interval. If the central server stores only sensor data associated with the reporting interval, then each time a user query the sensor data database for sensor data over a larger time interval, the database will have to retrieve a large amount of data and the central server will have to process the large amount of data retrieved into the time interval requested by the user. The time to execute query would be really slow, making it impractical and inefficient to perform real-time or continuous monitoring.

In embodiments of the present invention, the data collection engine 150 is configured to generate aggregated sensor data at time intervals that are of interest to users in practice. For example, hourly data or daily data may be more useful to a building maintenance staff monitoring the conditions of the building. When a query is made to the sensor data database for the hourly data, the database retrieves the aggregated hourly sensor data and can return the query result quickly and the central server does not have to process the retrieved data to provide the query result. In this manner, real-time monitoring of the sensor data is possible as the central server is able to return query result quickly by using the aggregated sensor data.

In other embodiments, the multi-level aggregated sensor data generated by the data collection engine and stored in the sensor data database may be advantageously used when the sensor data needs to be recalibrated. In particular, the data collection engine 150 uses calibration data associated with each sensor to calibrate the sensor readings received. However, the calibration data values for a sensor may change or may be updated over time. In some cases, it may be advantageous to re-calculate previously calibrated sensor data using updated calibration data values so as to improve the accuracy of historic sensor data. Although the central server 102 of the distributed sensor system 100 stores the raw sensor data, recalibrating the sensor data using the raw sensor data may be too computational intensive. In embodiments of the present invention, the central server 102 performs sensor data recalibration using aggregated sensor data stored in the sensor data database 108. The recalibration process using aggregated sensor data can be faster and less computationally intensive without appreciable loss of data accuracy. For example, the central server 102 may use the 1-hour aggregated sensor data for the recalibration process instead of the 1-second raw sensor data. Significant reduction in computation is realized without loss of data quality as the 1-hour data typically provides sufficient granularity for most practical applications.

In embodiments of the present invention, the data collection engine 150 further includes a recent reading cache memory 158. Recent reading cache memory 158 stores summarized sensor data to enable quick query of frequently requested sensor data. The summarized data includes sensor data associated with common or frequently requested queries, such as last hour of sensor data. With the recent reading cache memory 158 storing summarized sensor data, the summarized sensor data can be accessed quickly without requesting the data from the sensor data database 108. The recent reading cache memory 158 is optional and may be omitted in some embodiments of the present invention. However, in embodiments of the present invention, the recent reading cache memory 158 provides summarized sensor data which may be advantageously applied to improve the sensor data calibration.

In particular, as raw sensor data is being received, the sensor data converter 154 processes the raw sensor data by converting the raw sensor data to a physical unit and then calibrating the converted sensor data. As described above, the sensor data calibration can be more accurate in some cases when the temperature and/or humidity and/or pressure experienced by the sensor at the sampling time is taken into consideration in the calibration computation. In some embodiments, the sensor data converter 154 may query the sensor data database 108 for the recent temperature and/or humidity and/or pressure data, such as requesting aggregated temperature and/or humidity data for a recent time period from the sensor data database 108. However, database query tends to be slow and increased number of queries to the database is sometimes undesirable. Thus, in embodiments of the present invention, the recent reading cache memory 158 stores summarized temperature data, summarized humidity data, and/or summarized pressure data for a given recent time period, such as last 10 minutes or most recent 60 minutes. The time period can be variable and adjusted by the data collection engine to store the desired amount of recent data in the cache memory. The summarized temperature, humidity, and/or pressure data are stored in the cache memory 158. In this manner, the sensor data converter 154 can retrieve the recent temperature and humidity data from the recent reading cache memory 158 quickly when needed for calibration calculation. The sensor data calibration process at the data collection engine can be run more efficiently. In other embodiments, the recent reading cache memory 158 also store recent sensor data readings for removing sensor cross-sensitivity during calibration.

Figure 3:
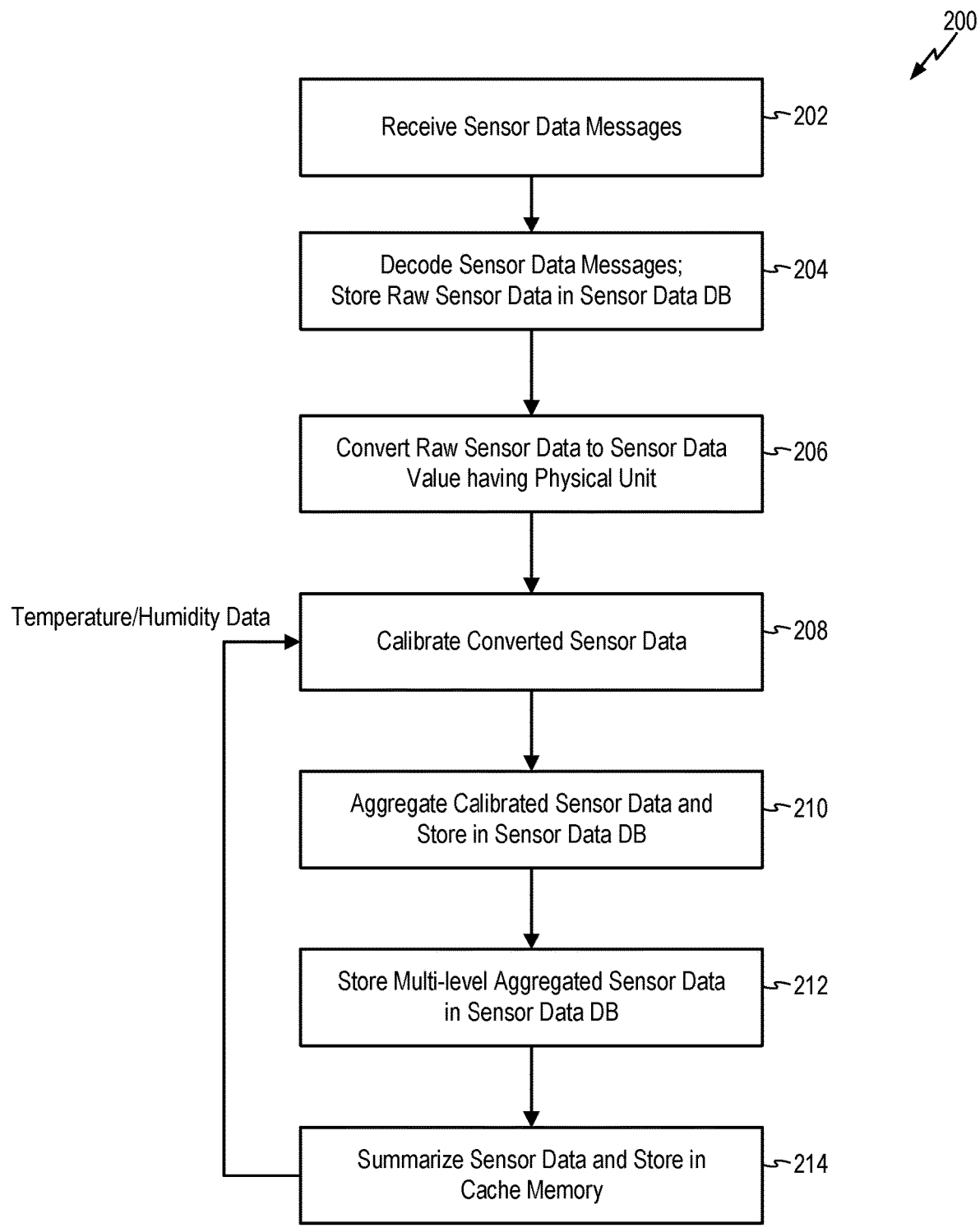
FIG. 3 is a flow chart illustrating a data collection method in embodiments of the present invention.

FIG. 3 is a flow chart illustrating a data collection method in embodiments of the present invention. Referring to FIG. 3, a data collection method 200 may be implemented in the central server 102 of the distributed sensor system 100 in FIG. 1 to collect and process sensor readings generated by the sensors that are deployed in the installation. At 202, the data collection method 200 receives sensor data messages as each sensor in the field reports its sensor reading at each reporting interval. At 204, the data collection method 200 decodes the sensor data messages to obtain the raw sensor data. The decoded raw sensor data is stored in the sensor data database.

At 206, the data collection method 200 converts the raw sensor data received into a sensor data value having a physical unit for the sensor type. For example, the raw sensor data may be converted to a sensor data value in ppm or in percentage. Then, at 208, the converted sensor data is calibrated using calibration data associated with the respective sensor. The calibrated sensor data may be stored in the sensor data database. In one embodiment, the calibrated sensor data and the raw sensor data for each sensor reading are stored in the same document in the sensor data database.

At 210, the data collection method 200 aggregates the calibrated sensor data over one or more predetermined time intervals to generate aggregated sensor data. For example, the sensor readings may be generated at a 1-second interval. The data collection method 200 may aggregate the calibrated sensor data over a 1-minute interval, 1-hour interval, a daily interval and a weekly interval. Accordingly, the data collection method may generate multi-level aggregated sensor data. At 212, the multi-level aggregated sensor data is stored in the sensor data database. In one embodiment, the data collection method 200 aggregate sensor data for a second time interval using previously aggregated sensor data for a first time interval stored in the sensor data database where the first time interval is shorter than the second time interval. For example, the data collection method 200 may aggregate sensor data for a 1-hour interval by using previously aggregated 10-minute sensor data.

In some embodiments, the data collection method 200 further includes generating summarized sensor data (214). The summarized sensor data is generated for frequently requested sensor data and the summarized sensor data is stored in a cache memory for quick access. In some embodiments, the data collection method 200 stores summarized temperature and humidity data for the recent time period in the local memory. The summarized temperature and humidity data can be assessed during the calibration process to improve the accuracy of the sensor data calibration. In other embodiments, the data collection method 200 stores summarized sensor data for removing sensor cross-sensitivity during calibration.

Scalable Distributed Stateless Processing

In most implementations, the distributed sensor system of the present invention will be deployed with a large number of installed sensor nodes and additional sensor nodes may be installed over time. Thus, the data collection system should be capable of handling a large amount of incoming data and also be scalable so that additional processing resources can be added as more sensors are being installed. In embodiments of the present invention, the data collection system and method of the present invention implements scalable distributed stateless processing to handle the large volume of input data and to also enable the data collection system to be scaled up easily as additional sensors are deployed in the distributed sensor system.

More specifically, the data collection engine 150 implements distributed processing using multiple software processes run on one or more processors to handle the large amount of data. For instance, each of the sensor data writer 152, the sensor data converter 154 and the sensor data aggregator 156 may be implemented using multiple software processes where the software processes are run on the same core of a processor, on separate cores of a processor or on separate processors. In this manner, the processing tasks are distributed over multiple software processes to increase the processing efficiency and processing capacity of the data collection engine. Furthermore, the data collection engine 150 implements stateless processing to achieve scalability. In the present description, stateless processing refers to multiple parallel software processes that do not use a central management and each software process operates independently without requiring information about the previous processing stage. Furthermore, the software processes do not communicate with each other and each software process is unaware of the other software processes. Another aspect of the stateless processing is that specific sensor data is not always routed to the same software process. In operation, data from the same sensor will be processed by multiple distributed software processes and therefore each distributed software process will manage a partial state of each sensor. The sensor data related to the partial state will be written independently to the sensor data database by each distributed software process and later may be combined to a single state. With the use of distributed stateless processing, when more processing power is needed, the data collection engine 150 can simply add additional parallel software processes to handle the additional demand.

Figure 4:
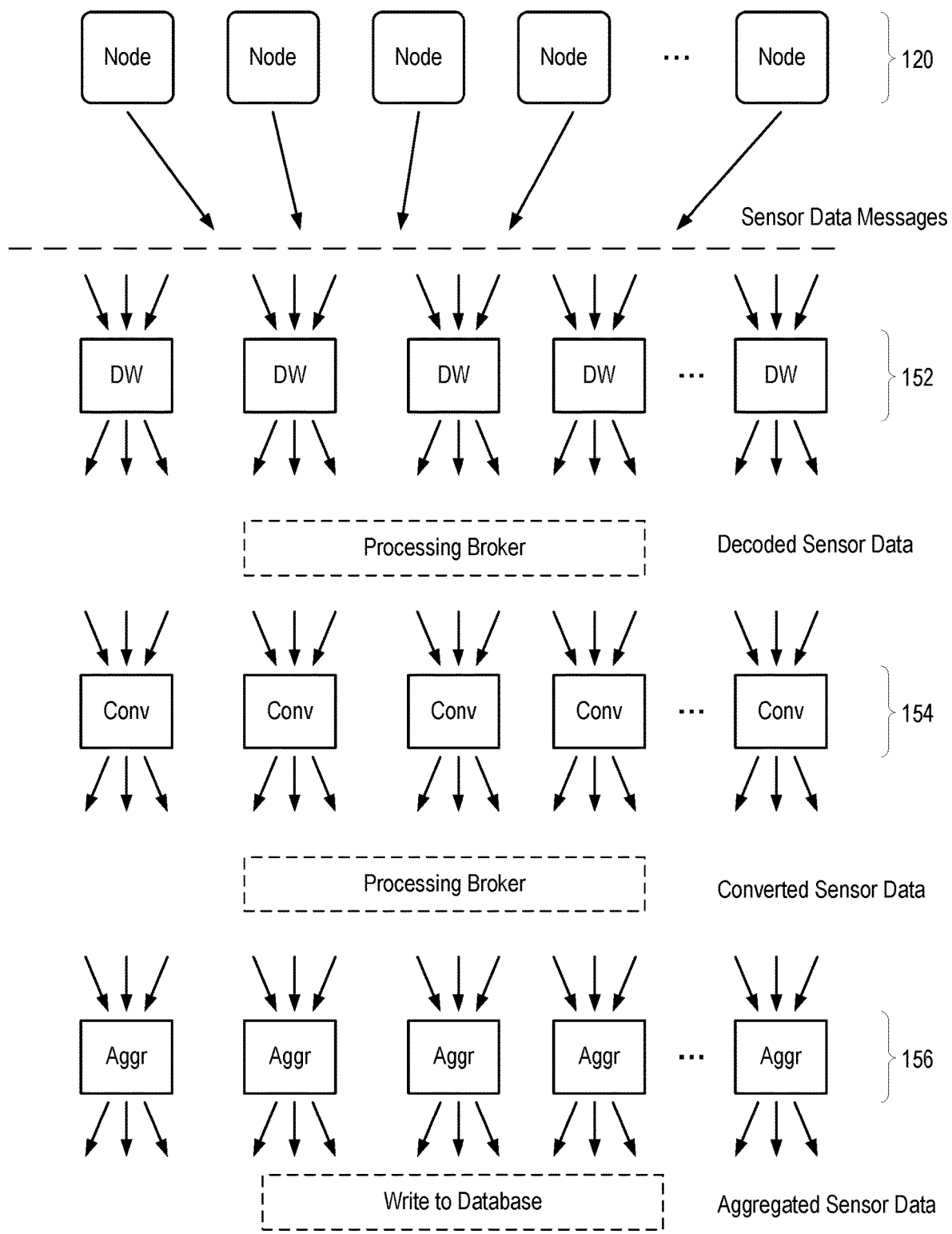
FIG. 4 is a representative figure illustrating the implementation of the scalable distributed stateless processing in the data collection engine of FIG. 2 in embodiments of the present invention.

FIG. 4 is a representative figure illustrating the implementation of the scalable distributed stateless processing in the data collection engine of FIG. 2 in embodiments of the present invention. Referring to FIG. 4, multiple sensor nodes 120 deployed in an installation report sensor data messages periodically. The sensor data messages are transmitted over a data network to the central server 102 and received by the data collection engine 150. At data collection engine 150, each processing stage is implemented using distributed parallel software processes running on one or more processors. More specifically, each software process represents a many-to-many connection between endpoints. At each processing stage, incoming data is fan out to allow any available software process to operate on the data. The processing of data is stateless, that is, the data is processed at each processing stage without regard to the previous processing state.

Thus, as shown in FIG. 4, the sensor data writer 152 is implemented using multiple software processes DW running on one or more processors, the sensor data converter 154 is implemented using multiple software processes Conv running on one or more processors, and the sensor data aggregator 156 is implemented using multiple software processes Aggr running on one or more processors. Accordingly, the incoming sensor data messages are pushed to any available sensor data writer software processes DW. The decoded sensor data generated by the sensor data writer processors are then pushed to the next processing stage, that is, the sensor data converter 154. After processing by the processors Conv at the sensor data converter, the converted sensor data is pushed to the sensor data aggregator 156 for further processing. The operation of the scalable distributed stateless processing may be described as having a processing broker between adjacent processing stages. The processing broker distributes the processing from one stage to another stage to realize a many-to-many type processing at each processing stage. The processing broker is illustrative only and may not be needed in some implementations. In one embodiment, the distributed stateless processing in the data collection engine is implemented using zeromq (ØMQ) which is a high-performance asynchronous messaging library with applications in scalable distributed or concurrent applications.

When the data collection system is implemented using distributed stateless processing, the data collection system is scalable as additional software processes or processors can be added in parallel when processing demand increases. Thus, the distributed sensor system can be expanded by deployment of additional sensors and the data collection system can be readily scaled up to handle the increased volume of continuous real-time sensor data.

Method to Combine Partially Aggregated Sensor Data

When the data collection system utilizes distributed and stateless processing, the sensor data aggregator includes multiple software processes running on one or more processors to process the aggregation of the sensor data. Because of the distributed and stateless processing, each software process Aggr may receive a portion of the sensor data that needs to be aggregated together. Thus, each software process Aggr end up generating partially aggregated sensor data.

For example, as shown in FIG. 4, multiple software processes Conv are used to process and calibrate the sensor data and multiple software processes Aggr are used to aggregate the sensor data. In operation, a set of sensor data values for the same sensor within the same time interval to be aggregated together may end up being processed by two software processes Aggr, each software process aggregating a unique portion of the sensor data values within that time interval. Thus, each software process generates partially aggregated sensor data. In one example, when 1-minute aggregated sensor data for a sensor is to be generated, a first software process Aggr may be available to aggregate sensor data values for some of the 1-second data and another software process Aggr may be available to aggregate the remaining 1-second sensor data values for that same minute interval. Each software process Aggr aggregates a portion of the sensor data values for the sensor for the desired 1-minute time interval. When a user wishes to query the sensor data database for the 1-minute aggregated sensor data, the central server would have to retrieve all of the partially aggregated sensor data and process the partially aggregated sensor data to generate the desired 1-minute aggregated sensor data. In some cases, the central server may perform on-the-fly aggregation and aggregate the partially aggregated sensor data to generate the desired 1-minute aggregated sensor data.

In embodiments of the present invention, the central server 102 includes an aggregation combiner 170 (FIG. 2) to combine partially aggregated sensor data in the sensor data database 108. In some embodiments, the aggregation combiner 170 is formed as part of the sensor data aggregator 156 of the data collection engine 150. In embodiments of the present invention, the aggregated sensor data is stored in the sensor database with an aggregation indicator. The aggregation combiner 170 is run periodically to search for partially aggregated sensor data in the sensor data database 108 based on the value of the aggregation indicator. The aggregation combiner 170 combines the partially aggregated sensor data belonging to the same time interval into a complete aggregated sensor data. The complete aggregated sensor data is then stored for future queries. In this manner, partially aggregated sensor data are combined before user query of the sensor data is received.

FIG. 5 illustrates an example of a sensor data document for storing aggregated sensor data in the central server in embodiments of the present invention. Referring to FIG. 5, a sensor data document 250 for storing aggregated sensor data includes identify information for the sensor from which the sensor data originates. For example, the identifying information may include the Node ID of the sensor node, the location identifier (Loc ID) of the sensor node, and the sensor ID. The sensor data document 250 further includes a time-stamp associated with the sensor data. In the present example, the sensor data is time-stamped by the Minute value and also the Period value. The Minute value identifies the minute to which the sensor data belongs and is identified by date, hour and minute values. The Minute value also identifies the sensor data as being a 1-minute aggregated sensor data. The sensor data document will have other time-stamp indicators, such as 10-Minute and Hour, for aggregated sensor data of other time intervals. The Period value is used to classify the sensor data based on a particular period of interest. In the present example, the Period value is a date value. Accordingly, the Period value can be used to retrieve sensor data taken on the same day.

Finally, the sensor data document 250 includes the sensor readings. In the present example, the sensor data document 250 stores the converted sensor data in the physical unit as well as the raw sensor data before conversion and calibration. Furthermore, when the sensor data document 250 stores aggregated sensor data, the sensor data document stores a maximum sensor data value, a minimum sensor data value, and the average sensor data value of the aggregated data values over the aggregation time interval. The sensor data document also stores the sum of the sensor data values being aggregated and the sample size.

The sensor data document 250 is tagged with an aggregation indicator "Agg ID" used to indicate the aggregation status of the document. In the present embodiment, when the sensor data has only been partially aggregated, the Agg ID has a non-zero value. On the other hand, when the sensor data has been completely aggregated, the Agg ID has a zero value or no value (i.e. the absence of any indicator value). Therefore, by examining the aggregation indicator value, the aggregation combiner can determine if the sensor data document contains partially aggregated data or completely aggregated data.

Figure 6:
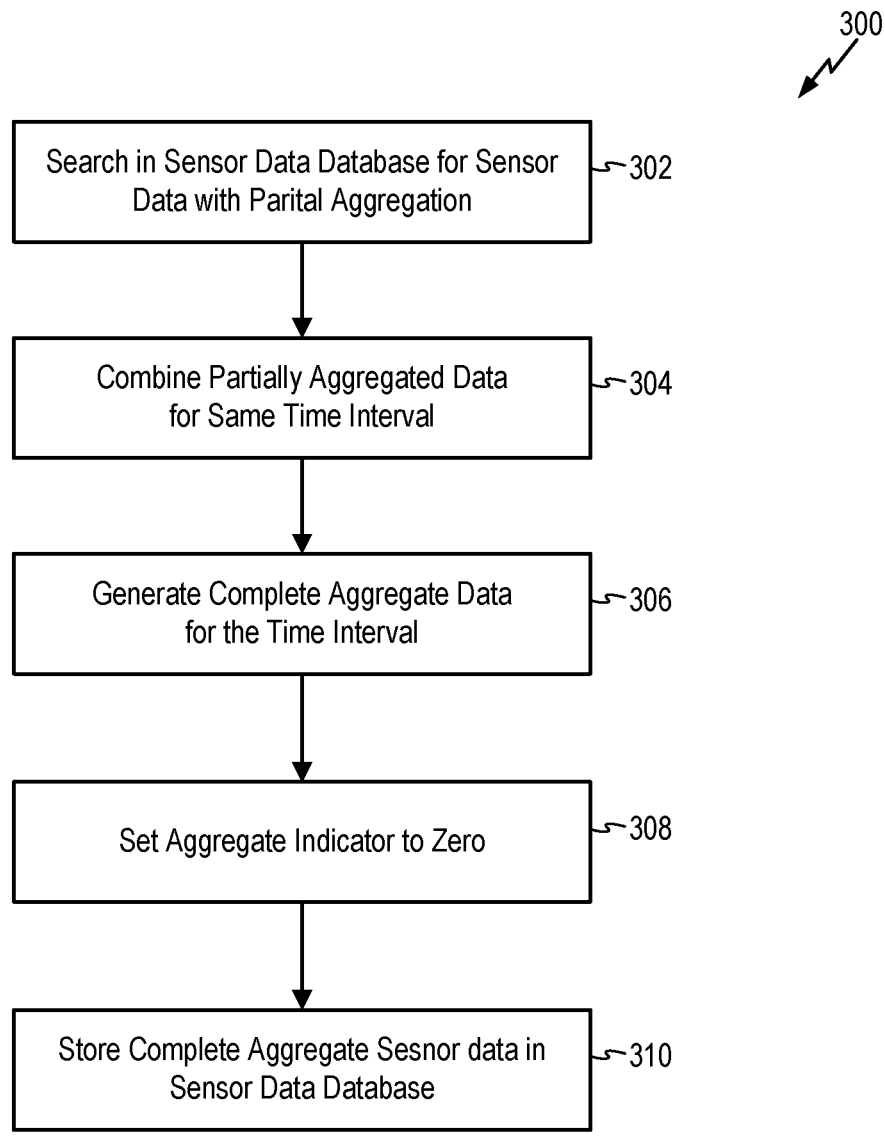
FIG. 6 is a flow chart illustrating a method to combine partially aggregated sensor data in embodiments of the present invention.

FIG. 6 is a flow chart illustrating a method to combine partially aggregated sensor data in embodiments of the present invention. Referring to FIG. 6, a method 300 may be implemented in the central server or the data collection engine of the central server of the distributed sensor system to combine sensor data that may have been partially aggregated. At 302, method 300 searches in the sensor data database for aggregated sensor data with a given time-stamp and with the aggregation indicator (Agg ID) set to a first value indicating partially aggregated data. For example, method 300 may search for 1-minute aggregated sensor data that has the date of 2013 Sep. 11 and a time of 11:14. If the aggregation indicator (Agg ID) is set to the first value, such as a non-zero value, then method 300 recognizes that aggregated sensor as being a partially aggregated sensor data. In this manner, method 300 collects all the partially aggregated sensor data for the same 1-minute interval.

At 304, method 300 combines the partially aggregated sensor data for the same time interval, e.g. the same 1-minute interval. In the present description, combining the partially aggregated sensor data refers to averaging the sensor data over all of sensor readings for that time interval. Because each partially aggregated sensor data may have a different sample size, accuracy of the combined aggregation is ensured only by averaging the original sensor data values, not by averaging the computed averages of the partial samples. In one embodiment, method 300 uses the summed value in each sensor data document to perform the computation to simplify the averaging operation. When the summed value and the sample size are available, method 300 only needs to add up all the summed values of the partially aggregated sensor data and divide by the total sample size. In this manner, method 300 generates the complete aggregated sensor data for that time interval (306).

At 308, method 300 generates the aggregated sensor data document for the complete aggregated sensor data and sets the aggregation indicator (Agg ID) to a second value, such as zero or no value (i.e. absence of any indicator value), to indicate that the sensor data is a complete aggregation. At 310, the sensor data document with the complete aggregated sensor data is stored in the sensor data database.

Sensor Data Query Method

With the deployment of the distributed sensor system, a large amount of sensor data for various sensor type can be collected from numerous locations over a wide geographic area. With the large amount of sensor data collected, a user may wish to query the sensor data for information, such as to monitor trends or to detect abnormalities. In embodiments of the present invention, a sensor data query method is provided to enable the sensor data to be queried quickly and easily and to present meaningful query result to the query requests. In embodiments of the present invention, the sensor data query method applies intelligence to interpret the query request and present query results that are meaningful for displaying sensor data. In some embodiments, the sensor data query method displays query results in a geospatial context. In one embodiment, the sensor data query method displays query results by presenting one set of sensor data in comparison with other sets of sensor data in a geospatial context. In one embodiment, the sensor data query method is implemented in a data query engine 180 in the central server 102, as shown in FIG. 2.

In particular, sensor data is more meaningful to a user when the desired sensor data is displayed in comparison with other related sensor data. In embodiments of the present invention, the sensor data query method applies Boolean logic to interpret a query request to generate a query result that shows the desired sensor data in comparison with related sensor data. In some embodiment, when a query request including one or more selection parameters is received, the sensor data query method determines a combination of logical AND operations and logical OR operations to be applied so as to yield meaningful query results.

In embodiments of the present invention, the sensor data query method specifies a query using four selection parameters: locations, location types, sensors and time. The "locations" selection parameter identifies the geographic location of interest and may include broad and fine geographic location identifications. In one embodiment, the locations selection parameter includes identifications of Cities, Buildings within each City, and Rooms and Areas within each Building. In some embodiments, the "locations" selection parameter can be specified by a latitude/longitude coordinate pair. The "locations" selection parameter can be made to select a geographic area with varying degree of granularity, such as an entire City or a room in a building of a city. That is, the "locations" selection parameter can be specified by choosing a city, and/or a building, and/or a room or space within the building. Default values are used when the user does not select specific "locations" parameters.

The "location types" selection parameter identifies various types of premises or areas within a building. In one example, the "location types" used in the sensor data query method can include Stairway, Hallway, Printer, Outdoor, Office, Phone room, Gym, Auditorium, Conference Room, Lab, Lounge, Open Space, Server Room, Open Office, Cafeteria, Cubicle, Lobby, and Kitchen. The "sensors" selection parameter identifies the sensor types being deployed. In one example, the sensor types used in the sensor data query method can include air quality sensors such as $CO_2$, $O_2$, CO, $CH_2O$, $NO_2$, HCHO, particulate matter, and volatile organic compound (VOC), and also environmental sensors such as humidity, light, temperature, sound and vibration sensors. The "time" selection parameter can include predefined time ranges and also a user-specified time range.

For example, when the query request selects sensor data for a single location ("Building A"), the sensor data query method interprets the request and provides sensor data for the requested location with sensor data for different location types (rooms, hallways, stairs) at that location separately displayed. Alternately, if the location only has one location type, then the sensor data query method interprets the request and provides sensor data for the requested location ("Building A") as well as nearby locations or similar locations nearby (e.g. "Buildings B and C"). In this manner, the sensor data for the requested location is displayed in comparison with sensor data from nearby or similar locations.

In another example, when the query request selects sensor data for two selection parameters, the sensor data query method interprets the request and provides query result showing sensor data meeting both selection parameters (AND logic) or sensor data meeting one of the selection parameters (OR logic), depending on the values of the selection parameters. The sensor data query method interprets the request and the selection parameters to provide a query result that presents a comparison of sensor data.

For example, when a query request includes a geographical location (e.g. "Office Building A in San Jose") as a selection parameter, then the sensor data query method provides the sensor data for the whole building as the search result with the sensor data for different location types at that location ("Office Building A") separately displayed. That is, the query result will display sensor data for the conference rooms, the offices, the hallways, the stairs, etc. of the whole building separately so that the sensor data for different location type within that building are compared against each other.

In another example, when a query request includes a large geographical location (e.g. "All Office buildings in New York") and a location type (e.g. "conference room"), then the sensor data query method provides the sensor data for the selected location type in all of the buildings in the selected geographical area (AND operation). In the present example, the sensor data query method will provide the sensor data for all the conference rooms in all the office buildings in New York.

In yet another example, when a query request includes a specific location (e.g. "Office Building B") and a specific location type (e.g. "Lobby"), then the sensor data query method provides the sensor data for the selected location and sensor data for the location type in any buildings (OR operation). In the present example, the sensor data query method will provide the sensor data in Office Building B and sensor data in all Lobbies in all other buildings. The OR operation is used in this query because there may not be a lobby in the selected office location. The sensor data query method uses the OR operation so that meaningful query result is generated for the user.

In another example, the sensor data query method provides query results including all sensor types when no specific sensor type is selected (OR operation). When the query request specifies a sensor type, then the sensor data query method provides query results including only the selected sensor type (AND operation).

In embodiments of the present invention, the sensor data query method presents query result in a graphical display with the horizontal axis being a time range and the vertical axis being the value of the sensor data. In some embodiments, the sensor data query method presents the query result with a fixed vertical scale for the vertical axis. Regardless of the range of the sensor data being displayed, the vertical scale for the vertical axis for each sensor type is fixed so that relative sensor data values are meaningful. For example, when the query result for sensor data at a location returns sensor data values all having very small absolute values, the sensor data is displayed on the fixed vertical scale to show that the sensor data values are small. On the other hand, when the query result for the same sensor data at another location returns sensor data values all having very large data values, the sensor data is displayed on the fixed vertical scale to show that the sensor data values are large. When a fixed vertical scale is used to display sensor data, the query results presented to users become meaningful and not obscured by extreme sensor values.

In another embodiment, the sensor data query method presents query results with the optimal value overlaid on the graphical display. In other embodiments, the sensor data query method presents query results with the minimum or maximum desired value overlaid on the graphical display.

Figure 7:
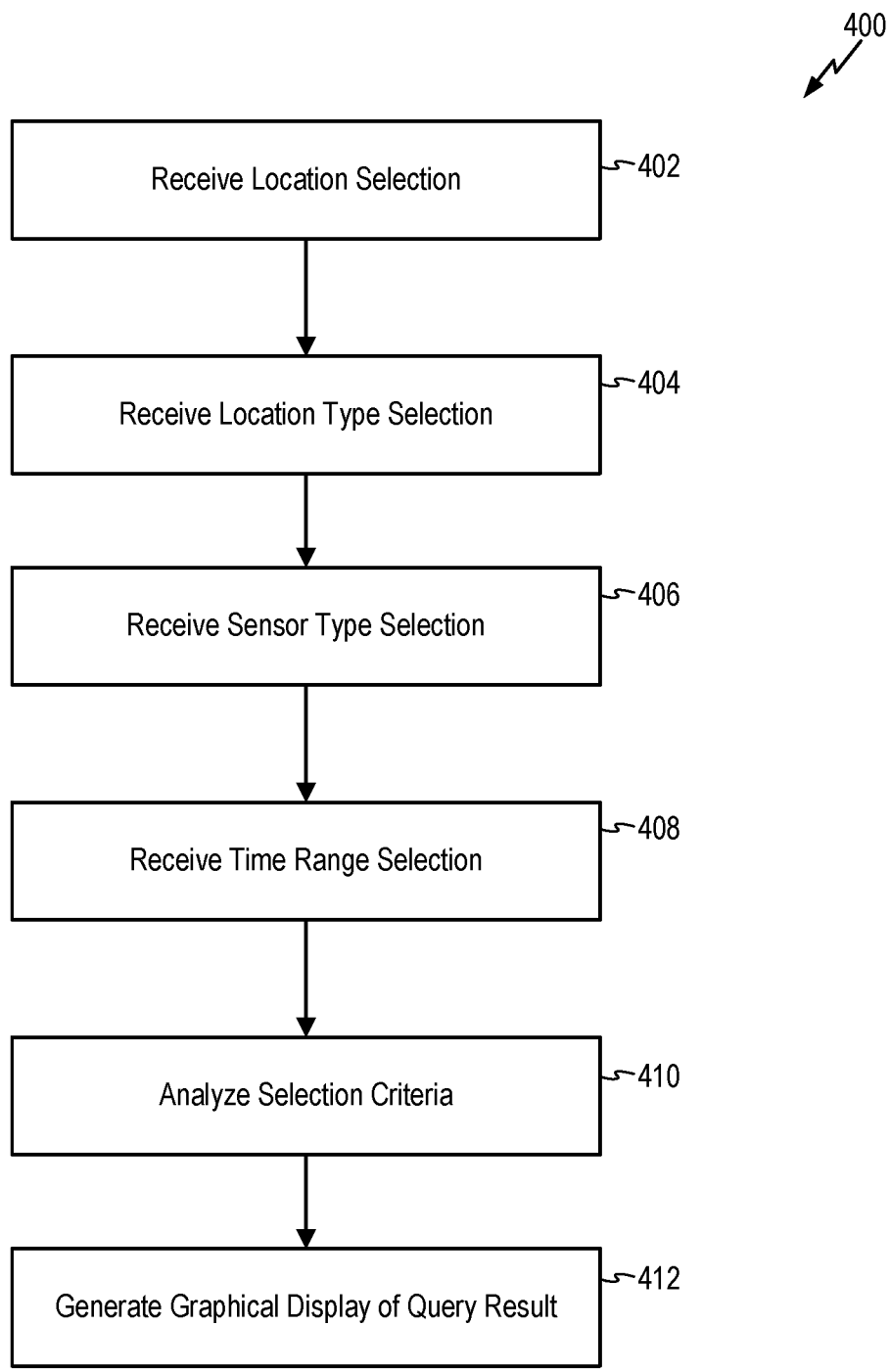
FIG. 7 is a flow chart illustrating the sensor data query method according to one embodiment of the present invention.
Figure 9:
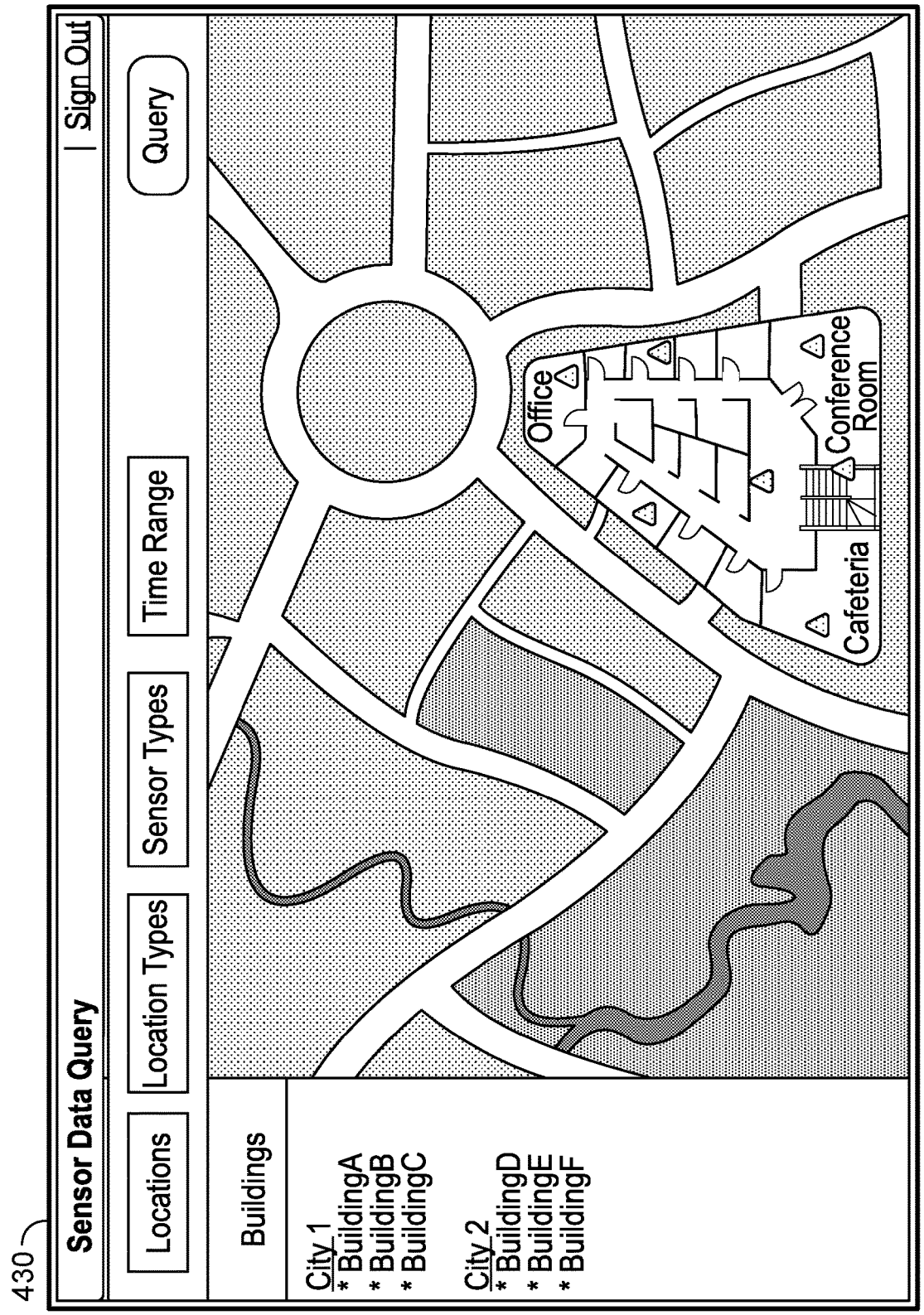
Figure 10:
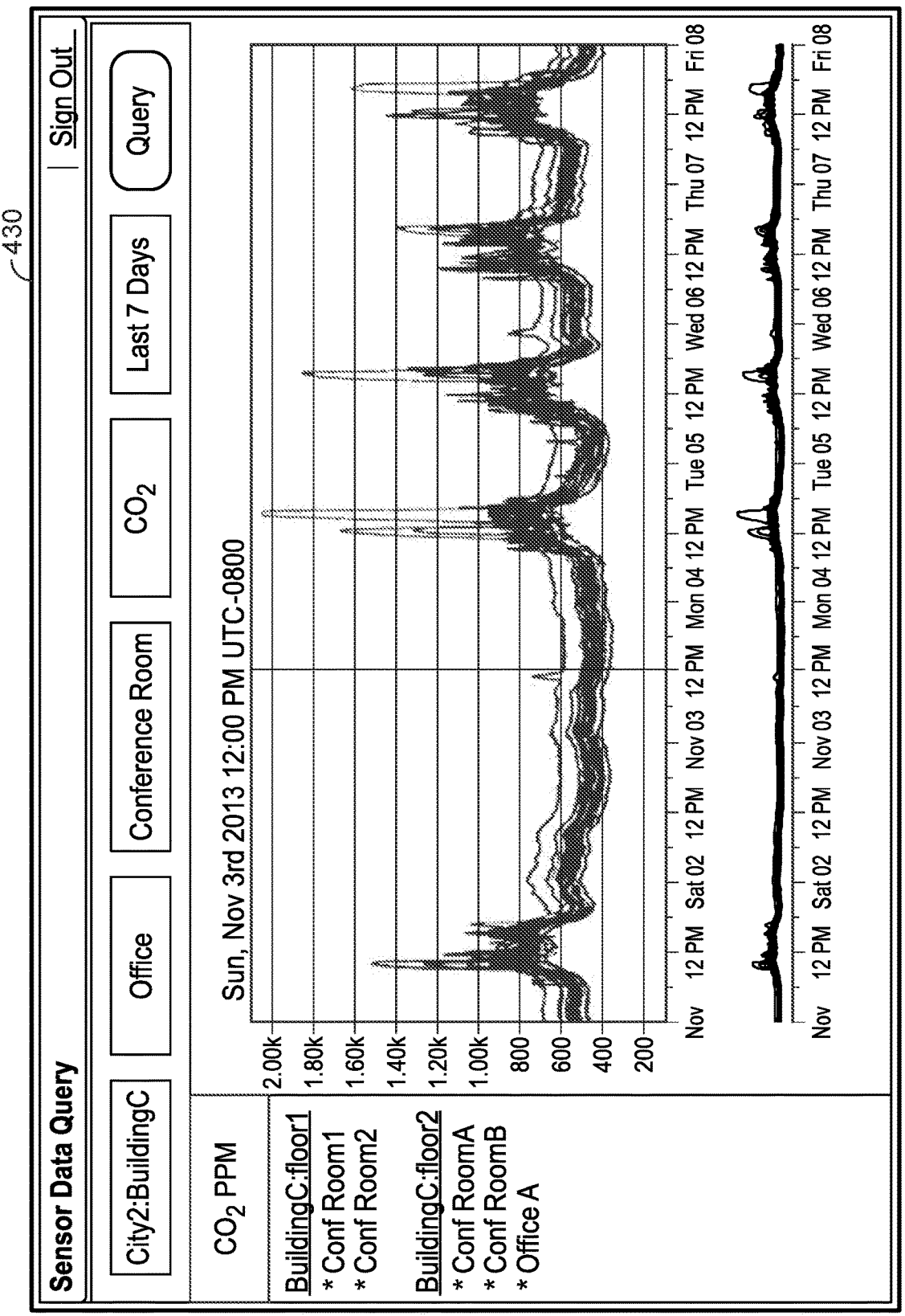

FIG. 7 is a flow chart illustrating the sensor data query method according to one embodiment of the present invention. FIGS. 8, 9 and 10 illustrate a user interface for performing sensor data query using the sensor data query method according to embodiments of the present invention. Referring to FIGS. 7-10, a sensor data query method 400 starts with a query request is formulated using the user interface 430 shown in FIG. 8. In the present example, the user interface 430 provides selection parameters including locations, location types, sensor types and time range. In the present illustration, "locations" refer to geographic locations or a place such as cities, buildings within each city, parks or other structures within each city, and "location types" refer to different types or kinds of premises, such as hallway, office, outdoor, gym, conference room and cafeteria. In the present illustration, "sensors" refers to air quality sensors such as $CO_2$, $O_2$, CO, $NO_2$, and also environmental sensors such as humidity, light, temperature and sound sensors. In the present illustration, "time range" includes a set of pre-determined time intervals of interest, such as Now (the most recent 60 minutes), Yesterday, Last 7 Days, etc. Custom date and time range can also be entered.

Using the user interface 430 to formulate a query request, the sensor data query method 400 receives a location selection from a list of locations (402). In one embodiment, the "location" parameter has a default value of all locations selected. Thus, when no location selection is made, method 400 selects all the location. Locations can be specified by a city name and further defined by a building name within each city. In some embodiments, method 400 may present a map image or a graphical display of geographic locations in the user interface to aid in the location selection.

At 404, the sensor data query method 400 receives a location type selection identifying one or more types of premises. The location type selection can be made from a list of location types provided by the user interface 430. In one embodiment, the "location type" parameter has a default value of all location type selected. Thus, when no location type selection is made, method 400 selects all the location types. Location types can include categories of location types, such as hallway, office, outdoor, gym, conference room and cafeteria. In some embodiments, method 400 may present a map image or a graphical display in the user interface to aid in the selection of the location types or a specific location type. For example, the map image may display the floor plan of a building with the locations of the deployed sensor shown by a sensor icon, as shown in FIG. 9. A selection of one or more location types can be made by clicking on the sensor icons.

At 406, the sensor data query method 400 receives a sensor type selection from a list of sensors. In one embodiment, the "sensor type" parameter has a default value of all sensors selected. Thus, when no sensor type selection is made, method 400 selects all the sensors available. For example, the list of sensors can include carbon dioxide ($CO_2$) sensors, oxygen ($O_2$) sensors, carbon monoxide (CO) sensors, temperature sensors and humidity sensors.

At 408, the sensor data query method 400 receives a desired time range. In some embodiments, the user interface 430 provides a list of pre-determined time range that is of common interest, such as Now (the most recent 60 minutes), Yesterday, Last 7 Days, etc. A custom date and time range can also be entered by specifying the start time and the end time. In one embodiment, the "time range" parameter has a default value of "Last 7 days" selected. Thus, when no time range selection is made, method 400 selects sensor data for the last 7 days.

At 410, the sensor data query method 400 analyzes the selection criteria. Based on the selection of location and location type, the sensor data query method 400 determines a combination of logical AND operations and logical OR operations to be applied to the selection criteria. The sensor data query method applies the selection criteria in a way so as to generate sensor data that can be compared with similar sensor data in a geospatial context. At 412, the sensor data query method 400 generates query result in the form of a graphical display of the selected sensor data.

Referring to FIG. 10, an example of a query result is illustrated. In FIG. 10, a query request is made for the $CO_2$ sensor data for City2, BuildingC. The selected location types include Office and Conference Room. The sensor data query method interprets the request as a logical OR operation and display sensor data for all offices and all conference rooms in BuildingC of City2. The selected time frame is Last 7 Days and thus the sensor data query method presents the sensor data for $CO_2$ for the last 7 days in the offices and conference rooms of BuildingC of City2. The sensor data display has a fixed vertical scale (200 K ppm for $CO_2$ sensor). As can be observed from the sensor data display, the conference rooms and offices are not occupied over the weekend and the rooms have low $CO_2$ level during those days. But during the work week (Monday to Friday), the $CO_2$ level in the rooms becomes high in the afternoon hours of each day.

In some embodiments, the sensor data query method provides a meaningful display of sensor data to enable hypothesis driven inquiry. A search request can be formulated based on a hypothesis and the sensor data query method can be used to display and compare sensor data to evaluate the hypothesis.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method for processing sensor data in a distributed sensor system, the distributed sensor system including a plurality of spatially distributed sensor nodes in communication with a data network, each sensor node comprising at least one sensor configured to measure an air quality parameter or an environment parameter, the method comprising:
   receiving sensor data messages sent by one or more sensors in the sensor nodes of the distributed sensor system;
   processing the sensor data messages using scalable distributed stateless processing to enable a data collection system of the distributed sensor system to be scaled up as additional sensors are deployed in the distributed sensor system, the processing being performed using multiple distributed parallel software processes running on one or more processor, wherein each of the multiple distributed parallel software processes do not communicate with each of the other of the multiple distributed parallel software processes and wherein each of the multiple distributed parallel software processes is unaware of the each of the other of the multiple distributed parallel software processes and wherein each of the multiple distributed software processes is configured to operate independently without requiring information about a previous processing state and to manage a partial state of a sensor such that sensor data related to the partial state is written independently to a sensor database;
   generating from the processing aggregated sensor data values associated with a first sensor and belonging to one or more aggregation time intervals,
   tagging each aggregated sensor data value with an aggregation indicator, the aggregation indicator having a first value to indicate that the aggregated sensor data value comprises a partially aggregated sensor data value having aggregated a unique portion of the sensor data values for the first sensor within a given aggregation time interval, and the aggregation indicator having a second value to indicate that the aggregated sensor data value comprises a complete aggregated sensor data value having aggregated all of the sensor data values for the first sensor within the given aggregation time interval; and
   storing in a memory the aggregated sensor data values tagged with the aggregation indicator;
   accessing the memory to retrieve aggregated sensor data values for a first time interval with the aggregation indicator set to the first value;
   combining the retrieved aggregated sensor data values to generate a complete aggregated sensor data value for the first time interval;
   tagging the complete aggregated sensor data value with an aggregation indicator having the second value; and
   storing in the memory the complete aggregated sensor data value tagged with the aggregation indicator having the second value.

2. The method of claim 1, wherein generating from the processing aggregated sensor data values associated with a first sensor and belonging to one or more aggregation time intervals comprises:
   averaging some or all of the sensor data values for the first sensor within a given time interval to generate the aggregated sensor data value for that given time interval.

3. The method of claim 1, wherein combining the retrieved aggregated sensor data values to generate a complete aggregated sensor data value for the first time interval comprises:
   averaging the sensor data values from the retrieved aggregated sensor data values to generate the complete aggregated sensor data value.

4. The method of claim 3, wherein generating from the processing aggregated sensor data values associated with a first sensor and belonging to one or more aggregation time intervals comprises:
   averaging some or all of the sensor data values for the first sensor within a given time interval to generate the aggregated sensor data; and
   storing a sensor data set with the aggregated sensor data value, the sensor data set comprising a maximum sensor data value, a minimum sensor data value and the average sensor data value over the given time interval, and further comprising a sum value of all sensor data values for the given time interval, and the number of samples for the given time interval.

5. The method of claim 4, wherein averaging the sensor data values from the retrieved aggregated sensor data values to generate the complete aggregated sensor data value comprises:
   adding the sum values in the retrieved aggregated sensor data values to generate a total sum value;

adding the numbers of samples in the retrieved aggregated sensor data values to generate a total number of samples; and dividing the total sum value by the total number of samples to generate the complete aggregated sensor data value.

6. The method of claim 1, wherein processing the sensor data messages using scalable distributed stateless processing to enable a data collection system of the distributed sensor system to be scaled up as additional sensors are deployed in the distributed sensor system, comprises:

decoding the sensor data messages to obtain decoded sensor data including sensor identifying information and sensor readings;

converting the sensor readings to sensor data values having physical units associated with the respective types of sensors that generated the sensor readings; and calibrating each sensor data value using calibration data associated with the sensor identified by the sensor identifying information accompanying the sensor readings.

7. The method of claim 1, wherein receiving sensor data messages sent by one or more sensors in the sensor nodes of the distributed sensor system comprises receiving sensor data messages at a sampling rate, the sampling rate being faster than the one or more aggregation time intervals.

8. The method of claim 1, wherein tagging each aggregated sensor data value with an aggregation indicator comprises:

tagging each aggregated sensor data value with the aggregation indicator having the second value to indicate that the aggregated sensor data value comprises a complete aggregated sensor data value having aggregated all of the sensor data values for the first sensor within the given aggregation time interval, the second value comprises a zero value or an absence of a value.

9. The method of claim 1, wherein storing in a memory the aggregated sensor data values tagged with the aggregation indicator comprises:

storing in a sensor data database stored in the memory the aggregated sensor data values tagged with the aggregation indicator.

10. A sensor data processing system for processing sensor data in a distributed sensor system, the distributed sensor system including a plurality of spatially distributed sensor nodes in communication with a data network, each sensor node comprising at least one sensor configured to measure an air quality parameter or an environment parameter, the sensor data processing system comprising:

a processor; and a memory coupled with the processor, wherein the memory is configured to provide the processor with instructions which when executed cause the processor to:

receive sensor data messages sent by one or more sensors in the sensor nodes of the distributed sensor system;

process the sensor data messages using scalable distributed stateless processing to enable the sensor data processing system to be scaled up as additional sensors are deployed in the distributed sensor system, the processing being performed using multiple distributed parallel software processes running on one or more processor, wherein each of the multiple distributed parallel software processes do not communicate with each of the other of the multiple distributed parallel software processes and wherein each of the multiple distributed parallel software processes is unaware of the each of the other of the multiple distributed parallel software processes and wherein each of the multiple distributed software processes is configured to operate independently without requiring information about a previous processing state and to manage a partial state of a sensor such that sensor data related to the partial state is written independently to a sensor database;

generate from the processing aggregated sensor data values associated with a first sensor and belonging to one or more aggregation time intervals, tag each aggregated sensor data value with an aggregation indicator, the aggregation indicator having a first value to indicate that the aggregated sensor data value comprises a partially aggregated sensor data value having aggregated a unique portion of the sensor data values for the first sensor within a given aggregation time interval, and the aggregation indicator having a second value to indicate that the aggregated sensor data value comprises a complete aggregated sensor data value having aggregated all of the sensor data values for the first sensor within the given aggregation time interval; and store in a memory the aggregated sensor data values tagged with the aggregation indicator;

access the memory to retrieve aggregated sensor data values for a first time interval with the aggregation indicator set to the first value;

combine the retrieved aggregated sensor data values to generate a complete aggregated sensor data value for the first time interval;

tag the complete aggregated sensor data value with an aggregation indicator having the second value; and store in the memory the complete aggregated sensor data value tagged with the aggregation indicator having the second value.

11. The sensor data processing system recited in claim 10, wherein the memory is further configured to provide the processor with instructions which when executed cause the processor to:

generate the aggregated sensor data values by averaging some or all of the sensor data values for the first sensor within a given time interval to generate the aggregated sensor data.

12. The sensor data processing system recited in claim 10, wherein the memory is further configured to provide the processor with instructions which when executed cause the processor to:

combine the retrieved aggregated sensor data values by averaging the sensor data values from the retrieved aggregated sensor data values to generate the complete aggregated sensor data value.

13. The sensor data processing system recited in claim 12, wherein the memory is further configured to provide the processor with instructions which when executed cause the processor to:

generate the aggregated sensor data values by averaging some or all of the sensor data values for the first sensor within a given time interval to generate the aggregated sensor data value; and store a sensor data set with the aggregated sensor data value, the sensor data set comprising a maximum sensor data value, a minimum sensor data value and the average sensor data value over the given time interval, and further comprising a sum value of all sensor data values for the given time interval, and the number of samples for the given time interval.

14. The sensor data processing system recited in claim 13, wherein the memory is further configured to provide the processor with instructions which when executed cause the processor to:
  average the sensor data values from the retrieved aggregated sensor data values by adding the sum values in the retrieved aggregated sensor data values to generate a total sum value;
  add the numbers of samples in the retrieved aggregated sensor data values to generate a total number of samples; and
  divide the total sum value by the total number of samples to generate the complete aggregated sensor data value.

15. The sensor data processing system recited in claim 10, wherein the memory is further configured to provide the processor with instructions which when executed cause the processor to:
  decode the sensor data messages to obtain decoded sensor data including sensor identifying information and sensor readings;
  convert the sensor readings to sensor data values having physical units associated with the respective types of sensors that generated the sensor readings; and
  calibrate each sensor data value using calibration data associated with the sensor identified by the sensor identifying information accompanying the sensor readings.

16. The sensor data processing system recited in claim 10, wherein the memory is further configured to provide the processor with instructions which when executed cause the processor to:
  receive sensor data messages sent by one or more sensors in the sensor nodes of the distributed sensor system at a sampling rate, the sampling rate being faster than the one or more aggregation time intervals.

17. The sensor data processing system recited in claim 10, wherein the memory is further configured to provide the processor with instructions which when executed cause the processor to:
  tag each aggregated sensor data value with the aggregation indicator having the second value to indicate that the aggregated sensor data value comprises a complete aggregated sensor data value having aggregated all of the sensor data values for the first sensor within the given aggregation time interval, the second value comprises a zero value or an absence of a value.

18. The sensor data processing system recited in claim 10, wherein the memory is further configured to provide the processor with instructions which when executed cause the processor to:
  store in a sensor data database stored in the memory the aggregated sensor data values tagged with the aggregation indicator.

* * * * *